United States Patent [19]

Guigan

[11] Patent Number: 5,077,013
[45] Date of Patent: Dec. 31, 1991

[54] MINIATURE LABORATORY FOR PERFORMING BIOLOGICAL ANALYSES BY CHEMICAL REACTION ON A SAMPLE OF BLOOD

[76] Inventor: Jean Guigan, 5 rue des Ursulines, 75005 Paris, France

[21] Appl. No.: 381,433

[22] Filed: Jul. 18, 1989

[30] Foreign Application Priority Data

Jul. 28, 1988 [FR] France .................. 88 10210

[51] Int. Cl.⁵ ............................................ G01N 21/11
[52] U.S. Cl. ........................................ 422/64; 422/72;
422/100; 436/45; 356/246; 356/427; 494/16
[58] Field of Search ............... 422/64, 72, 100, 102;
436/45; 356/246, 427; 494/16

[56] References Cited

U.S. PATENT DOCUMENTS

| | | | |
|---|---|---|---|
| 4,135,883 | 1/1979 | McNeil et al. | 494/21 |
| 4,390,499 | 6/1983 | Curtis et al. | 422/72 |
| 4,814,282 | 3/1989 | Holben et al. | 422/72 |
| 4,865,810 | 9/1989 | Simon | 436/45 |

FOREIGN PATENT DOCUMENTS

2578054 8/1986 France .
2592170 6/1987 France .

Primary Examiner—Robert J. Warden
Assistant Examiner—Laura E. Collins
Attorney, Agent, or Firm—Sughrue, Mion, Zinn, Macpeak & Seas

[57] ABSTRACT

A miniature laboratory (1) for performing biological analyses comprises a block (2) supporting two concentric turntables (3 and 4). The top turntable (3) carries preparation cartridges (6) each intended to receive a blood sample and to deliver a calibrated quantity of plasma therefrom. The bottom turntable (4) carries analysis cartridges (40) for analyzing the plasma from the cartridges (60).

6 Claims, 14 Drawing Sheets

MINIATURE LABORATORY FOR PERFORMING BIOLOGICAL ANALYSES BY CHEMICAL REACTION ON A SAMPLE OF BLOOD

The present invention relates to a miniature laboratory for performing biological analyses by chemical reaction on a sample of blood.

BACKGROUND OF THE INVENTION

In French patent FR-A 84 18954 filed Dec. 20, 1985, the present Applicant describes a method of delivering a predetermined quantity of plasma from a sample of blood for analysis purposes. This method makes use of substantially rectangular cartridges which are rotated about themselves a certain number of times and which are subjected to a certain number of centrifuging operations in order to treat a few micrometers of blood and separate out one or more calibrated volumes of plasma. The plasma is intended to be analyzed in a device as described, in particular, in any of the following French patents: FR-A-84 16448, filed Oct. 26, 1984; FR-A-84 19719 filed Dec. 21, 1984; FR-A-85 04476 filed Mar. 26, 1985; and FR-A-85 04477 filed Mar. 26, 1985.

In all of the above cases, the method requires plasma to be transferred to the treatment device.

The object of the present invention is to overcome this drawback and provide a portable miniature laboratory enabling a doctor to perform analyses on a sample of blood under optimum conditions of simplicity and speed.

SUMMARY OF THE INVENTION

The present invention provides a miniature laboratory for performing biological analyses by chemical reaction on a blood sample, wherein the laboratory comprises a block containing electronic and mechanical components, and supporting two coaxial turntables:

a top turntable or "preparation turntable" provided with radial housings for supporting preparation cartridges each for delivering at least one calibrated dose of plasma from a blood sample, said housings being capable of being rotated about their own centers;

a bottom turntable or "analysis turntable", provided with a ring of recessed sectors suitable for supporting analysis cartridges, each being closed by a lid having a breakable skin and each having an internal liquid-receiving compartment separated by a fragile wall from a peripheral distribution compartment adjacent to a plurality of vertical reaction tubes containing solid reagents;

said bottom turntable being slightly larger in diameter than the top turntable so as to leave said peripheral reaction tubes visible;

and wherein the laboratory includes, in said block:

means for separately driving the two turntables, when distant from each other, in rotation about their common axis, either slowly or for centrifuging;

means for moving the top turntable into a low position against the bottom turntable, the top turntable being provided with piercing members level with said breakable skins in such a manner as to establish communication between the preparation cartridges and the liquid-receiving compartments of the analysis cartridges;

means for driving both turntables, when constrained to rotate together, about their common axis;

means for breaking said fragile wall;

an optical analysis reader module situated level with the path of said analysis tubes; and a programmed microcomputer.

In a preferred embodiment, said top turntable is provided with three preparation cartridges each capable of delivering two calibrated doses of plasma, and said bottom turntable is provided with six analysis cartridges, with the first three being intended for analyzing respective first doses and with the second three being intended for analyzing respective second doses.

Each analysis cartridge includes about ten reaction tubes, and is stored in sealed manner with a diluant in its liquid-receiving compartment.

Preferably, said preparation cartridge comprises a box closed by a lid, both made of transparent plastic material, said box comprising first and second end faces and first and second longitudinally-extending side faces, and being compartmented in such a manner as to present:

a blood sample receiving receptacle running along said first longitudinally-extending side face from said first end face, followed by an outlet channel in which a plasma storage channel and a red corpuscle storage cell terminate; and a measurement cell running along said second longitudinally-extending side face going from said first end face, said measurement cell being connected by a capillary tube firstly to a central plasma evacuation cell having an outlet orifice in the bottom of said box, and secondly to an overflow channel opening out into said plasma storage cell and then into an overflow receptacle, the end of the measurement cell opposite to said capillary tube being connected by a capillary duct to overflow cells which also open out into said overflow channel. In addition, said preparation cartridge may also have a longitudinal channel against said second longitudinally-extending face and at the outlets from said overflow cells opposite from the outlet communicating with said measurement cell, said longitudinal channel opening out into a plasma storage receptacle situated close to said second end face.

BRIEF DESCRIPTION OF THE DRAWINGS

An embodiment of the invention is described by way of example with reference to the accompanying drawings, in which.

DETAILED DESCRIPTION

Figure 1:
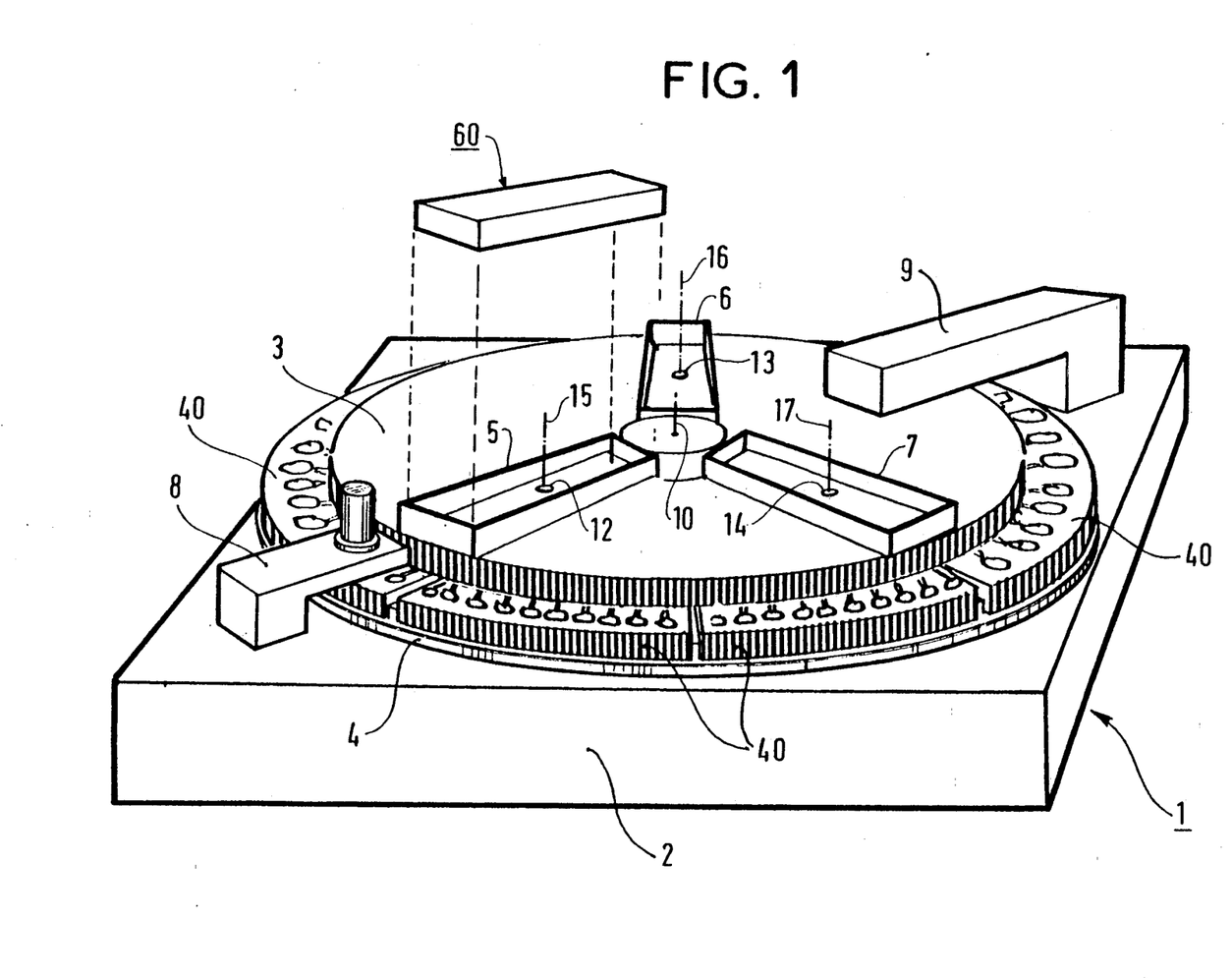
FIG. 1 is a highly diagrammatic perspective view of a miniature laboratory in accordance with the invention.

FIG. 1 is a highly diagrammatic representation of a miniature laboratory 1 in accordance with the invention and it is drawn nearly life-size. It comprises a rectangular block 2 containing mechanical drive elements and electrical circuits, and two circular turntables 3 and 4 disposed one on top of the other on top of the block 2 and suitable for rotating about their common axis 10. The top preparation turntable 3 includes three radial housings 5, 6, and 7 each in the form of a lid-less rectangular box, and each suitable for rotating about a respective central axis 15, 16, or 17. Each of the three housings can therefore take up the position shown in FIG. 1 or alternatively the position which can be derived therefrom by rotating the housing through 180° about its central axis 15, 16, or 17.

Figure 2:
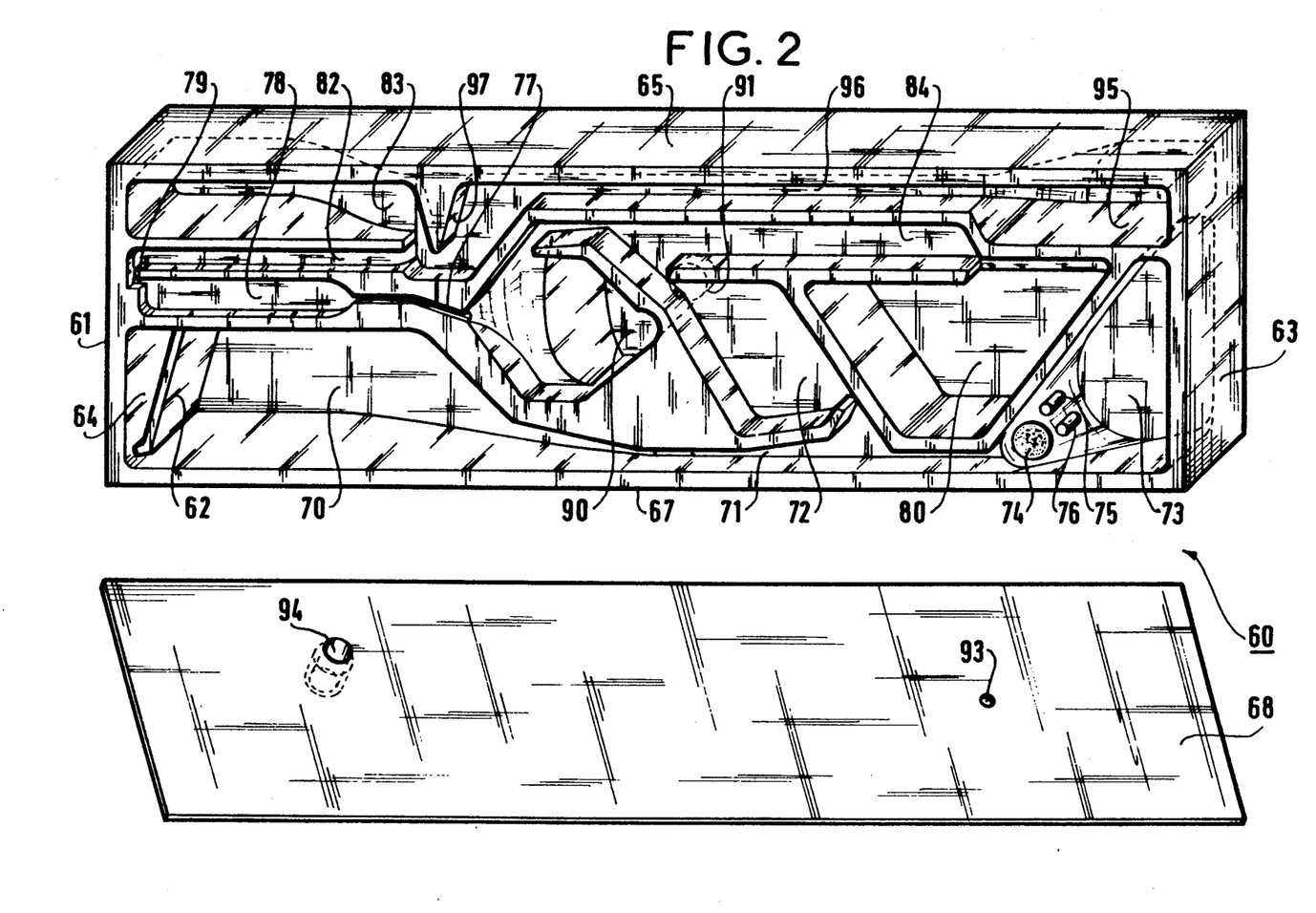
FIG. 2 is an exploded perspective view of a preparation cartridge belonging to the FIG. 1 laboratory.
Figure 10:
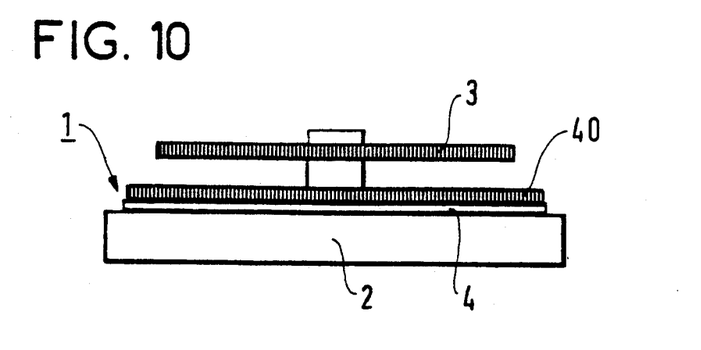
FIG. 10 is a diagrammatic elevation view of the FIG. 1 laboratory, with its top turntable raised.
Figure 11:
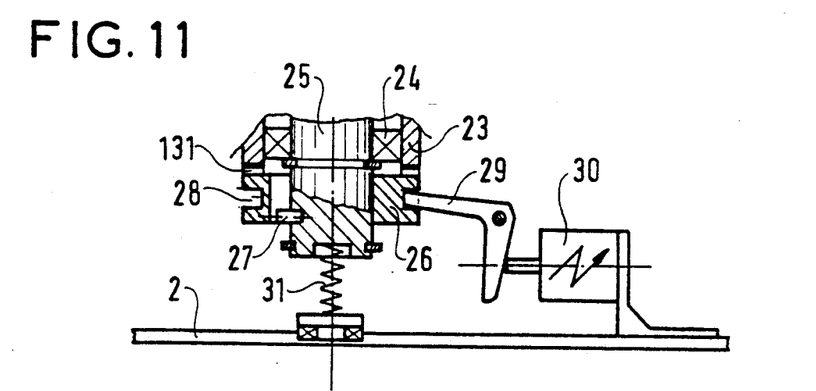
FIG. 11 is a diagrammatic fragmentary view showing the device for driving the top turntable of FIG. 10.

Each housing is intended to contain a preparation cartridge 60 as described in above-mentioned French patent number FR-A-85 18954, and as shown in FIG. 2 and described in greater detail below. As explained in greater detail below, the preparation turntable 3 may be in a lowered position as shown in FIG. 1 where it comes against the bottom analysis turntable 4 (see FIG. 12), or else it may be in a high or raised position as shown in FIG. 10, where it is disconnected from the turntable 4.

When in its high position, the turntable 3 is capable of rotating about its axis 10 independently from the turntable 4, whereas when it is in its low position, both turntables are constrained to rotate together about the common axis 10.

Figure 4:
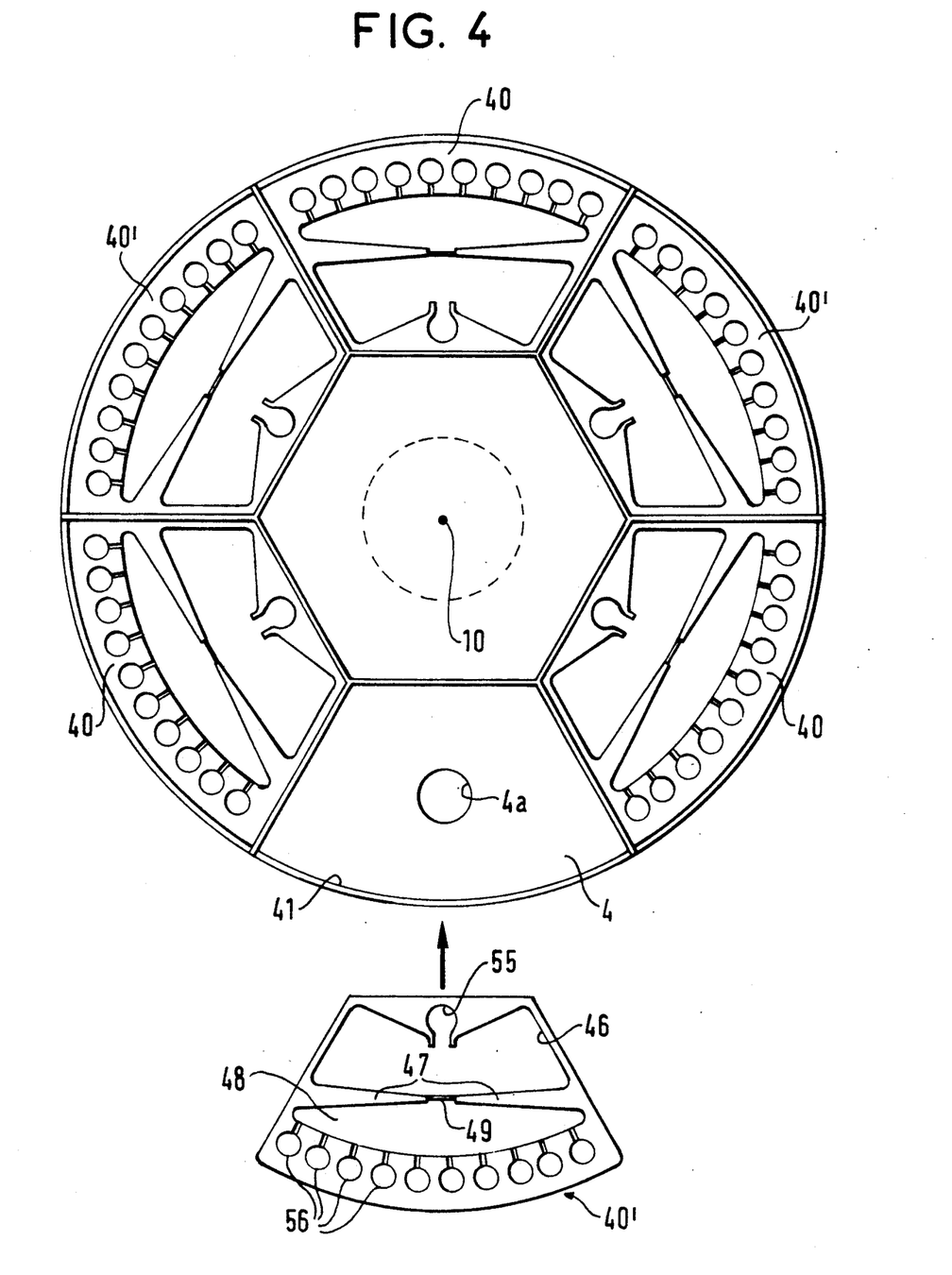
FIG. 4 is a diagrammatic plan view of the analysis turntable of the FIG. 1 laboratory.

The analysis turntable 4 is visible in greater detail in FIG. 4 and comprises six analysis cartridges 40 for receiving the plasma delivered by the preparation cartridges 60 for the purpose of chemical analyses. These cartridges 40 are described in greater detail below, as is the method in which they are put into communication with the preparation cartridges 60.

The miniature laboratory 1 also includes (see FIG. 1) an analysis reader module 8 situated level with the path of the periphery of the analysis turntable 4, and a module 9 suitable for rotating the housings 5, 6, and 7 about their respective axes.

FIG. 2 is an exploded perspective view of a preparation cartridge 60 for delivering two successive calibrated doses of plasma. It is made entirely out of transparent plastic material. It comprises a housing provided with a lid 68 having an orifice 64 via which a sample of blood is inserted therein, and also having a vent 93. Its end faces are referenced 61 and 63 and its longitudinally-extending side faces are referenced 65 and 67.

Figure 3A:
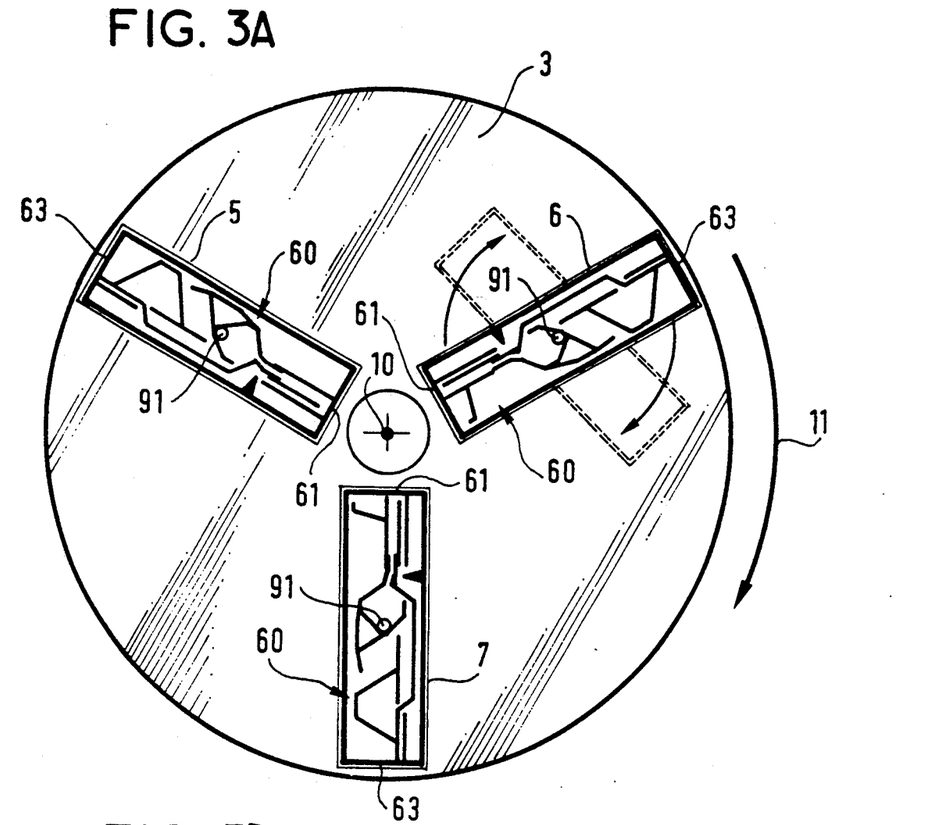
FIGS. 3A and 3B are diagrammatic plan views of the preparation turntable with its cartridges shown respectively in position A and in position B.
Figure 3B:
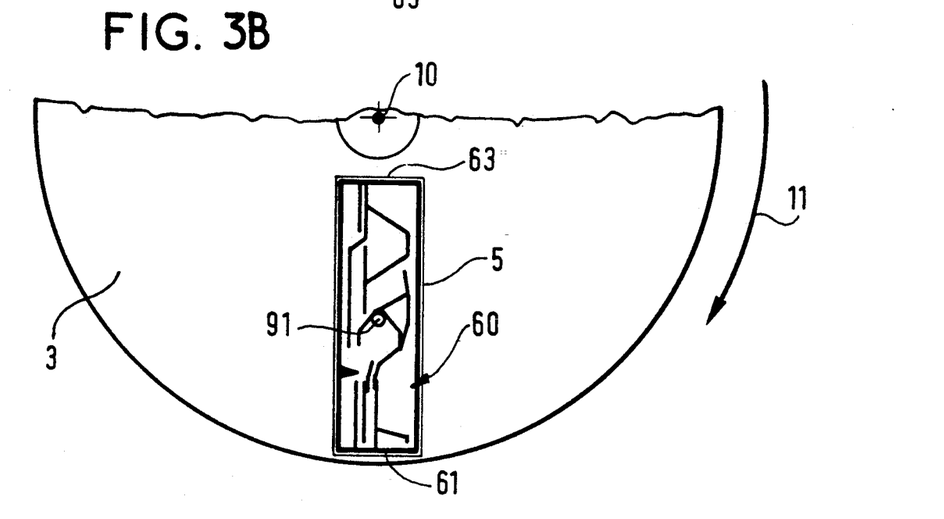

As can be seen in FIG. 3A, each preparation cartridge 60 is in radial position A when its end face 61 is the end face closer to the axis 10. In FIG. 3B, each preparation cartridge 60 is shown in its radial position B, i.e. with its end face 61 being close to the periphery of the turntable 3. Arrow 11 indicates the direction of rotation about the axis 10.

Returning to FIG. 2, it can be seen that the housing contains, running along its longitudinally-extending side face 67: a blood-receiving receptacle 70; an outlet channel 71 into which a plasma storage cell 72 opens out; and then a red corpuscle storage cell 73.

The receptacle 70 has an additional transverse wall 62 which partitions this receptacle in part and which defines an end compartment 64.

A small ball 74 made of weighted plastic material and associated with two retaining pegs 75 and 76 is provided in the vicinity of the orifice of the channel 71 in the cell 73.

The plasma storage cell 72 is connected firstly via a capillary tube 77 to a measurement cell 78 of calibrated volume, and secondly via an overflow channel 84 to an overflow receptacle 80.

With respect to the plasma storage cell 72, the measurement cell 78 is situated on the same side as the receiving receptacle 70, while the overflow receptacle 80 is situated on the same side as the corpuscle storage cell 73.

The measurement cell 78 is connected firstly via a capillary duct 79 to plasma overflow cells 82 and 83, and secondly via a capillary tube 77 to a central plasma evacuation cell 90 which opens out to the outside through an outlet orifice 91 situated in the bottom of the preparation cartridge 60.

Each orifice 91 is situated over an opening 12, 13, or 14 provided in the middle of the bottom of the housing 5, 6, or 7 in which it is received (see FIG. 1).

Figure 6:
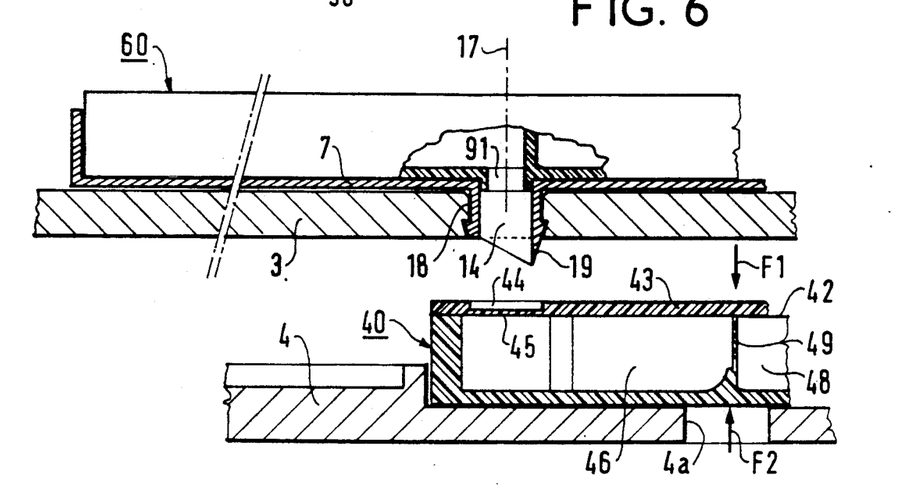
FIG. 6 is a section view on a larger scale showing how a preparation cartridge co-operates with an analysis cartridge when the two turntables supporting them are moved together.

FIG. 6 is on a larger scale and shows the respective dispositions of the turntable 3, the housing 7 with its opening 14, and the preparation cartridge 60 with its orifice 91. The turntable 3 has an opening 18 at this level which is provided at its bottom end with a piercing member 19 whose function is explained below.

Along the longitudinally-extending face 65 of the cartridge 60 (see FIG. 2) there are disposed, running from end face 61: an overflow cell 83; a duct 96; and a plasma storage receptacle 95 whose function is described below. A baffle or chicane 97 is provided in the duct 96 level with the inlet to the overflow cell 83.

As can be seen in FIG. 4, the bottom analysis turntable 4 has six recesses 41 each in the form of a circular sector and each intended to receive one analysis cartridge 40 having the same shape. There are six of these cartridges which are split up into two alternating series: three of them are referenced 40 and the other three are referenced 40'.

The first three cartridges operate on the first dose of plasma delivered by the three preparation cartridges 60 installed on the turntable 3, whereas the three second cartridges operate on respective second doses of plasma delivered thereafter by the same preparation cartridges 60, with the top turntable 3 then being displaced through 60° from its first position relative to the bottom turntable.

Figure 5:
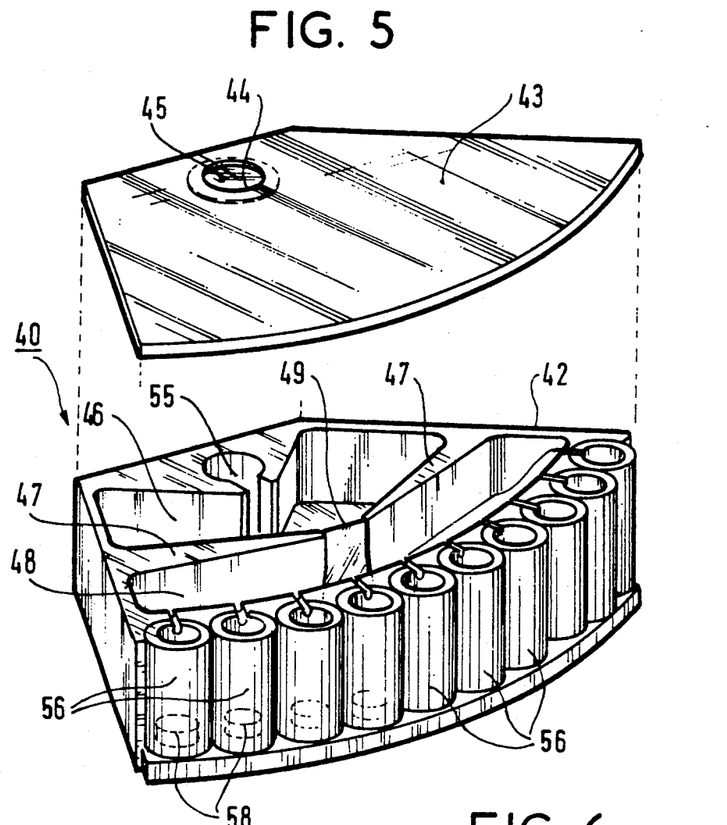
FIG. 5 is a diagrammatic exploded perspective view of an analysis cartridge disposed on the FIG. 4 analysis turntable.

As can be seen in FIG. 5, each analysis cartridge 40 is made of transparent plastic material and comprises a housing 42 which is closed by a lid 43 provided with an opening 44 that is closed by a breakable skin 45. This breakable skin is intended to be situated in line with the axis 17 of the coaxial openings 14, 91, and 18 in the top turntable (see FIG. 6), and in particular in line with the piercing member 19.

The housing 42 includes a compartment 46 close to the axis 10 and referred to as the "liquid-receiving" compartment 46, which compartment initially contains a diluant. The zone 55 in the compartment 46 is situated level with the breakable skin 45. The compartment 46 is separated by a wall 47 from a peripheral distribution compartment 48 which is adjacent to ten vertical reaction tubes 56. Each of the reaction tubes 56 preferably contains dry reagents 58. The wall 47 has a fragile middle zone 49 enabling the two compartments 46 and 48 to be kept apart during storage. However when the turntables 3 and 4 are put into place against each other (direction F1 in FIG. 6), a hammer (not shown and actuated by an electromagnet), serves to strike through an opening 40 provided in the turntable 4 (force F2) beneath the cartridge 60 in order to break the fragile zone 49.

FIGS. 7 to 13 are diagrams showing the mechanical components housed in the support block 2 for the turntables 3 and 4 and serving to drive them.

Figure 7:
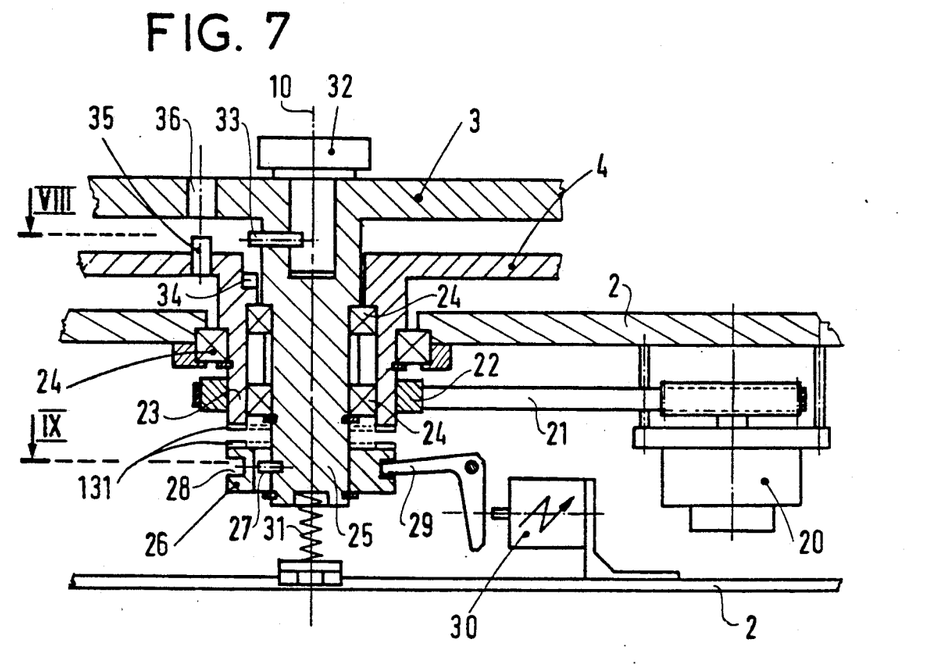
FIG. 7 is a diagrammatic view partially in section showing the mechanical means for driving the turntables.

In FIG. 7, there can be seen the top turntable 3 and the bottom turntable 4 together with their common axis of rotation 10, said turntables being shown disconnected from each other. A D.C. motor 20 is associated with an angle encoder for enabling the rotations of the turntables to be controlled, and is fixed to the block 2. It is associated with a transmission system including a cog belt 21 and a wheel 22 fixed to a hub 23 connected to turntable 4. Reference 24 is used for various bearings. In the position shown in FIG. 7, the turntables 3 and 4 are at a distance from each other; in other words, the turntable 3 is in its high or raised position, so the motor 20 can drive only the turntable 4.

The bottom end of the shaft 25 connected to the turntable 3 is fixed by means of a return spring 35 to the block 2. A clutch 26 (also visible in FIG. 9) is connected by a finger 27 to rotate with the shaft 25. It has a circular groove 28 co-operating with a two-position lever 29 under the control of an electromagnet 30.

When the lever 29 goes from the position shown in FIG. 7 to its high position, two toothed faces referenced 131 respectively on the hub 23 and on the clutch 26 come into mutual co-operation and both turntables 3 and 4 which, while still at a distance apart from each other, are driven simultaneously by the motor 20. This situation appears more clearly in associated FIGS. 10 and 11.

Figure 8:
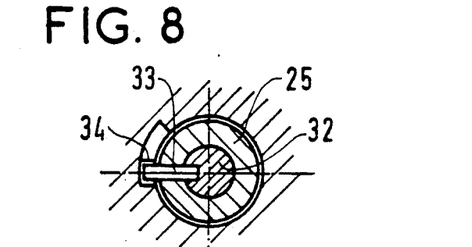
FIG. 8 is a section view on line VIII of FIG. 7.
Figure 9:
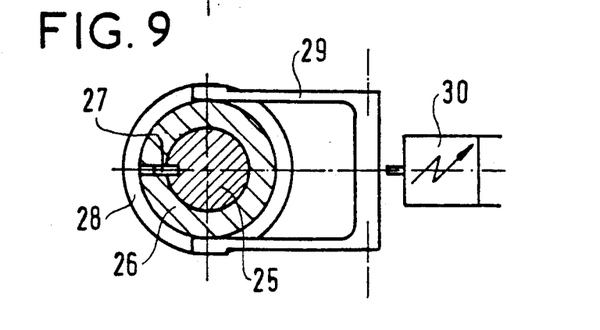
FIG. 9 is a section view on line IX—IX of FIG. 7.
Figure 12:
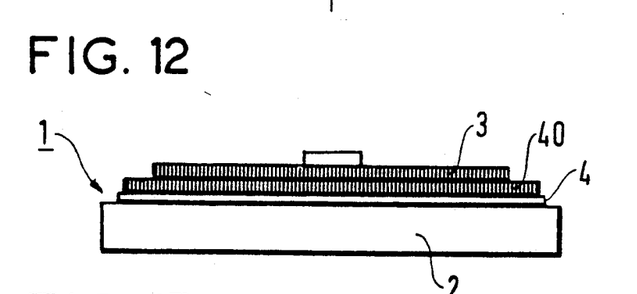
FIG. 12 is a diagrammatic elevation view of the FIG. 1 laboratory with its top turntable in its lowered position.
Figure 13:
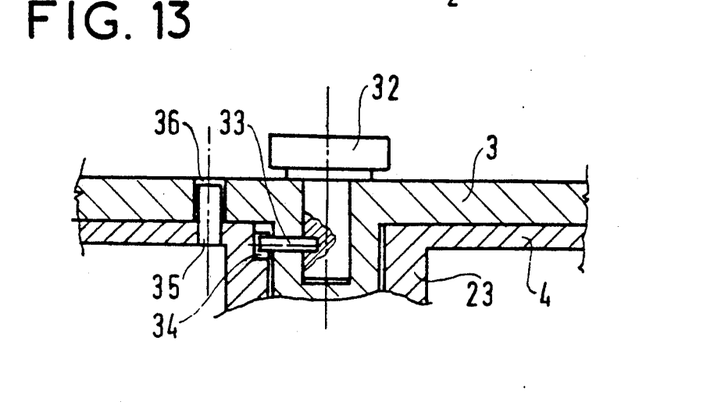
FIG. 13 is a diagrammatic fragmentary view of the device for driving the top turntable in FIG. 12.

In order to lower the turntable 3, as illustrated in FIG. 12, a central knob 32 is pressed down, which knob is connected to the shaft 25 via a finger 33 which is visible in FIGS. 7 and 8. The finger is locked in an orifice 34 provided in the hub 23, and a vertical peg 35 enters into a hole 36 provided for that purpose in the turntable 3. This gives rise to the position shown in FIG. 13. The turntables 3 and 4 are very accurately located relatives to each other and they are constrained to rotate together.

When pressure is applied to the knob 32 (see FIG. 6), all three piercing members 19 belonging to the top turntable 23 pierce the breakable skins 45 on the cartridges 40, which cartridges are thus put into communication with the preparation cartridges 60.

There follows a description of the utilization stages of a miniature laboratory of the invention.

Three analysis cartridges 40 are put into place in the recesses 41 of the lower turntable 4. Three preparation cartridges are put into place in the A position as shown in FIG. 3A in the turntable 3 while it is in its high position.

Figure 14:
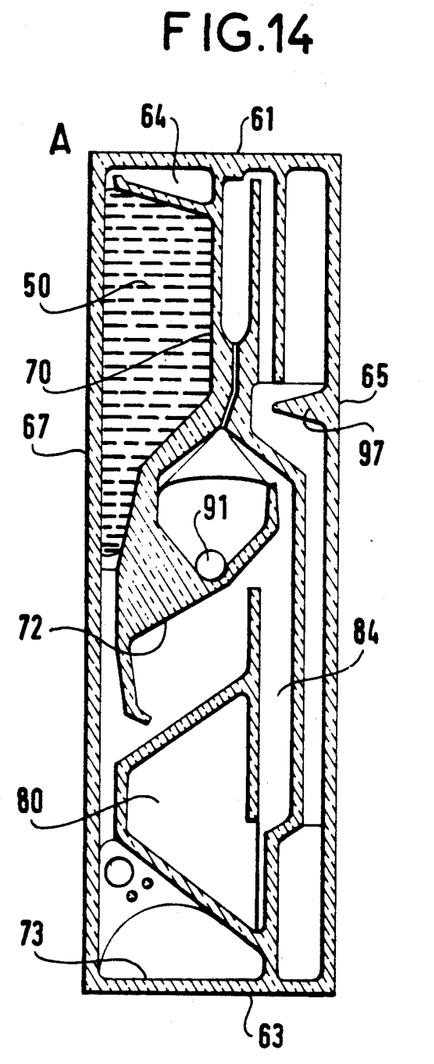
FIGS. 14 to 21 show the different implementation stages of a preparation cartridge for delivering a first dose of plasma.
Figure 15:
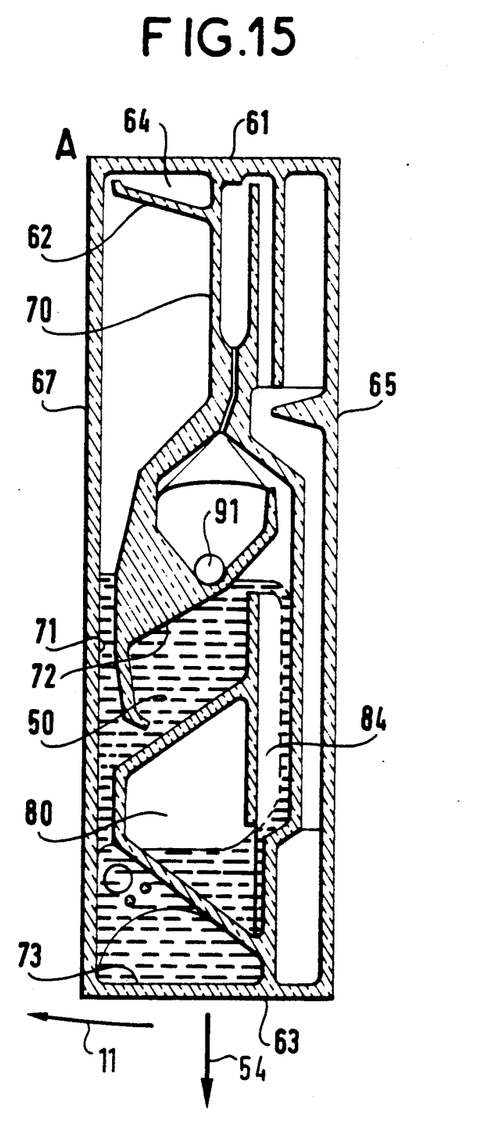
Figure 16:
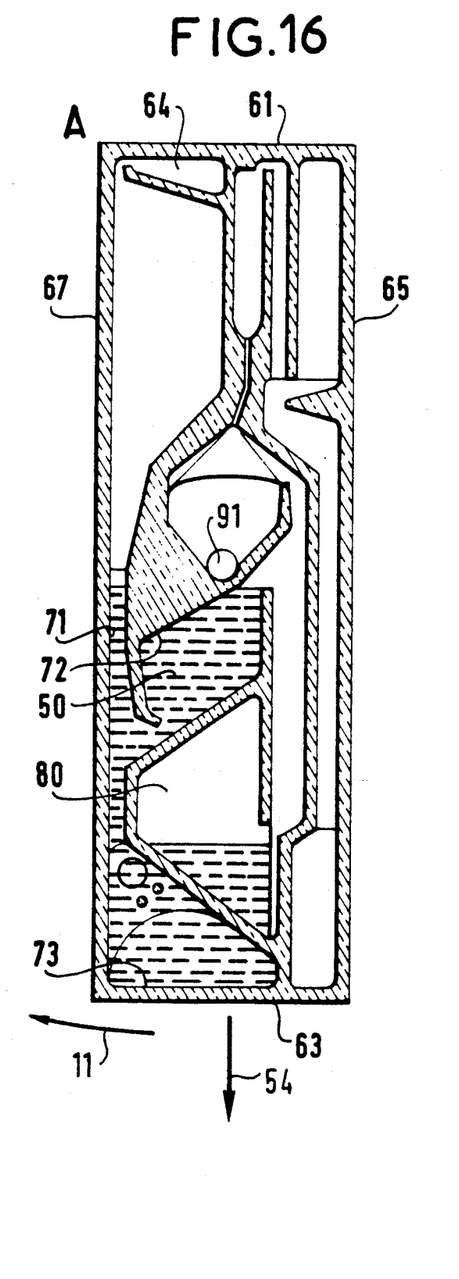
Figure 17:
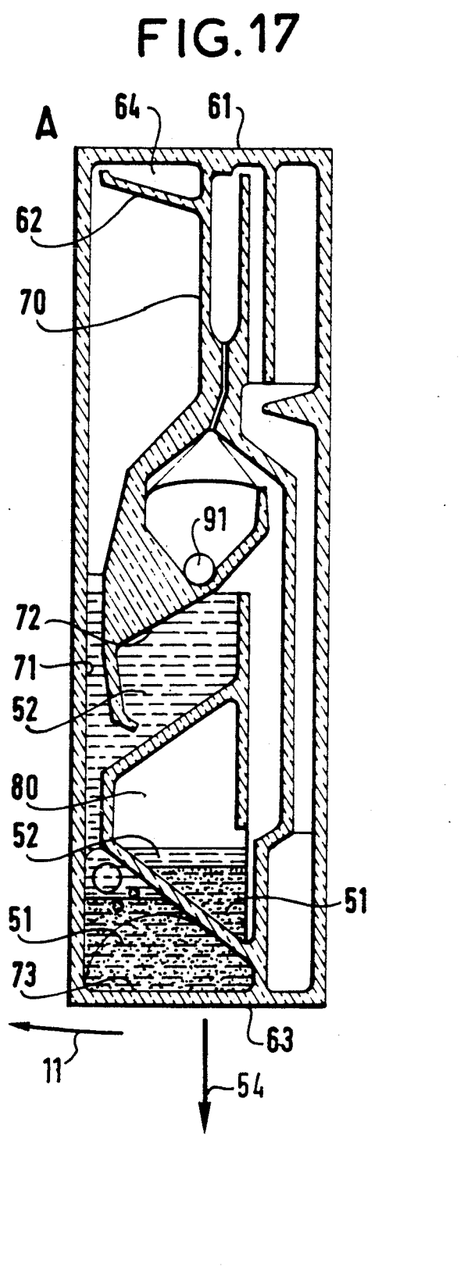

Attention is paid initially to cartridge 60 which is shown in FIG. 14 and into which the doctor has inserted a sample of blood 50 by means of a pipette. In FIG. 15, rotation 11 of the turntable 3 has begun and centrifugal force 54 has the effect of emptying the receptacle 70 via the channel 71 into the plasma storage cell 72, the cell 73, the overflow channel 84, and the overflow receptacle 80. FIG. 16 shows the state of the cartridge 60 at this moment. As rotation continues (FIG. 17) red corpuscles 51 are separated out and accumulate in the storage cell 73 and in the overflow receptacle 80. Plasma 52 is to be found in the cell 72, in the channel 71, and in the overflow receptacle 80.

Figure 18:
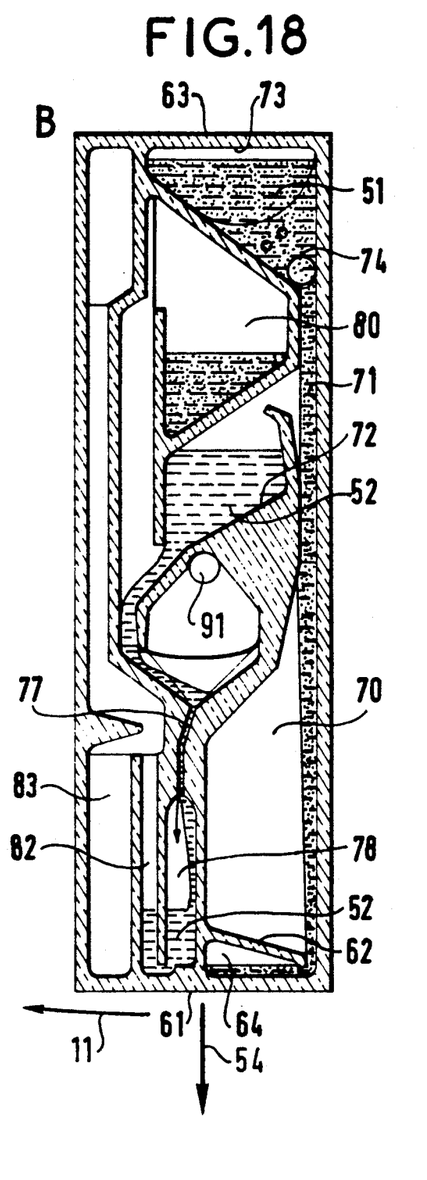
Figure 19:
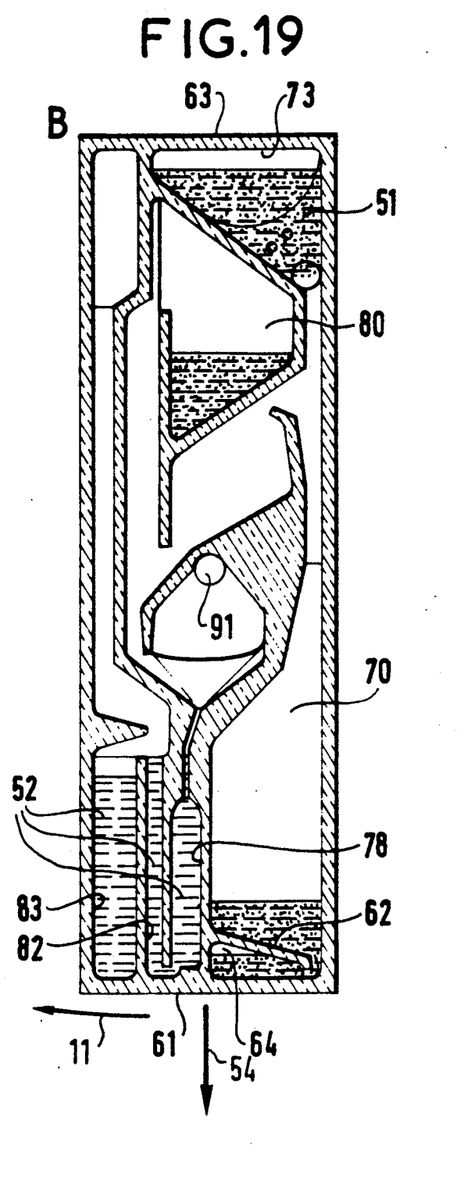

The cartridge 60 is then put into position B (FIG. 3B). At this moment, centrifugal force 54 empties the cell 72 via the capillary tube 77 (FIG. 18). Plasma initially fills measurement cell 78, and then overflow cells 82 and 83. This gives rise to the situation shown in FIG. 19.

Simultaneously, several of the red corpuscles present in the cell 73 manage to pass into the receptacle 70 and the compartment 64 in spite of the channel 71 being closed by the ball 74.

Figure 20:
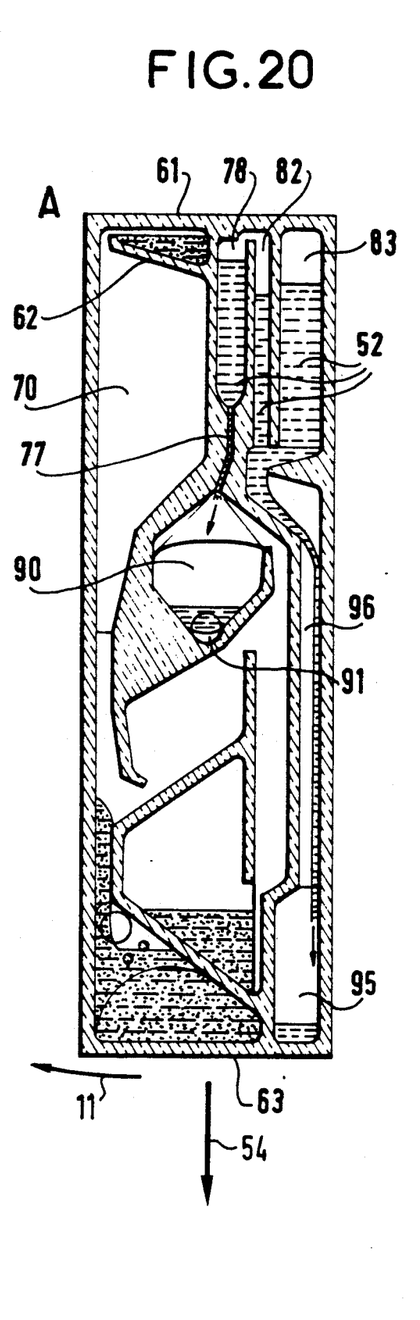
Figure 21:
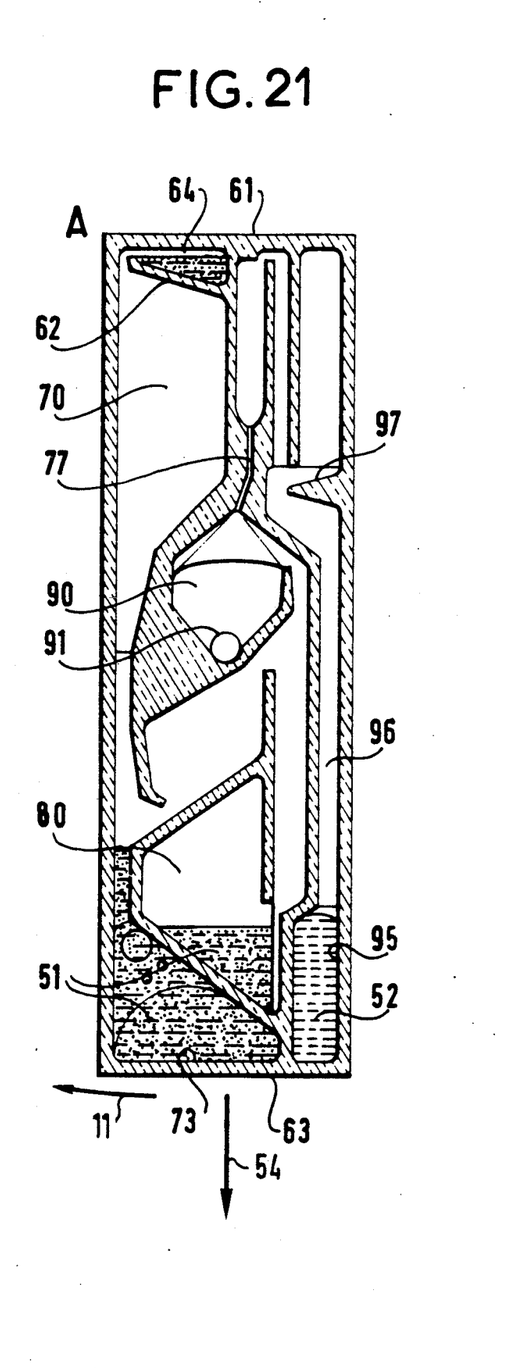

The cartridge 60 is then returned to position A (FIG. 3A) and pressure is applied to the knob 32 in order to lower the top turntable 3. Evacuation cell 90 of the cell 60 is thus put into communication with the liquid-receiving compartment 46 of the corresponding analysis cartridge 40 (see FIG. 6). At this moment, by virtue of the centrifugal force 54, a calibrated quantity of plasma 52 can be seen to pass from the calibrated cell 78 into the evacuation cell 90 via the capillary tube 77 (FIG. 20). This calibrated quantity is evacuated via the outlet orifice 91 (FIG. 21) in the cartridge 40. Simultaneously, excess plasma present in the overflow chambers travels via duct 96 into a plasma storage receptacle 95. The red corpuscles are stored in the cell 73, the overflow receptacle 80, and the compartment 64.

Figure 22:
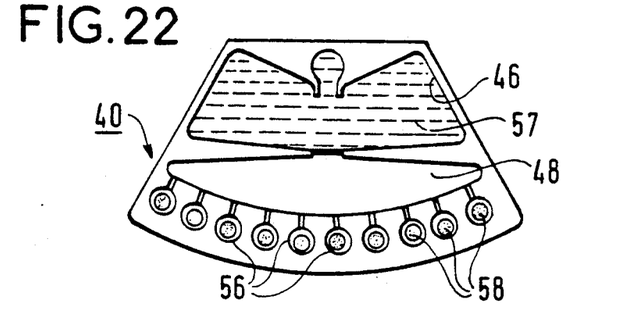
FIGS. 22 to 26 show the different implementation stages of an analysis cartridge.
Figure 23:
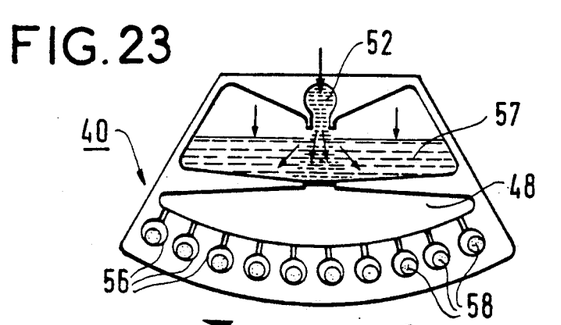
Figure 24:
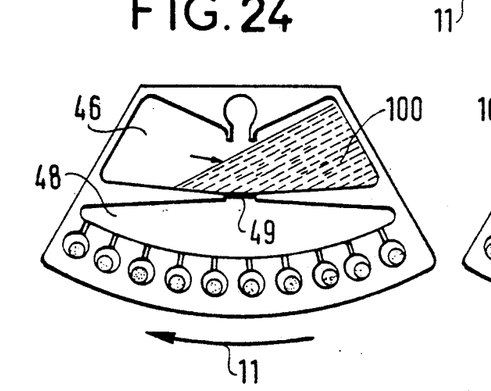
Figure 25:
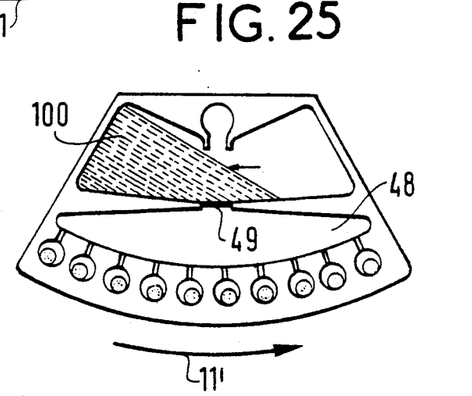

The situation in the cartridge 40 (see FIG. 22) which initially contained a diluant 57 in its liquid-receiving compartment 46 then corresponds to the situation shown in FIG. 23 in which the plasma 52 can be seen. At this moment suddenly reversing the direction of rotation of the turntable 4 repeatedly and several times over in the directions referenced 11 and 11' in FIGS. 24 and 25 causes the mixture 100 to be thrown from the compartment 46 towards the opposite two sides of this compartment. This ensures that the mixture 100 is homogeneous.

Thereafter, the fragile zone 79 is broken by a hammer blow applied in direction F2 of FIG. 6. Subsequently, the turntable 3 is advantageously disconnected from the turntable 4 which may be rotated on its own (compare the situation shown in FIG. 7).

Figure 26:
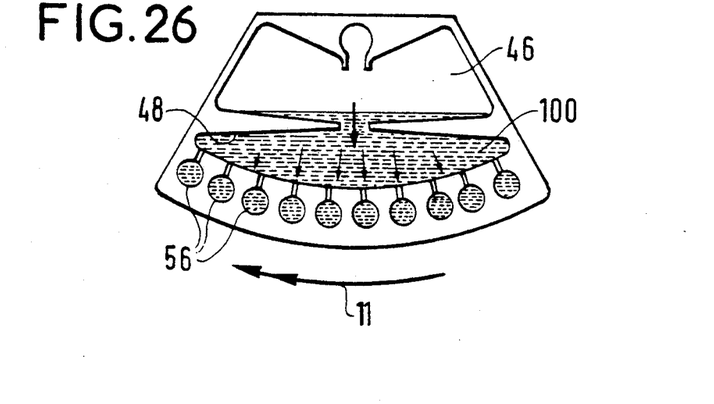

Once the fragile zone 49 has been broken, communication is established between the compartments 46 and 48, and a further centrifuging operation gives the mixture 100 access to the various reagents 58 contained in the reaction tubes 56 (see FIG. 26).

After a period of time determined by the nature of the reagents, the reader module 8 (see FIG. 1) specifies the nature of the reaction.

Figure 27:
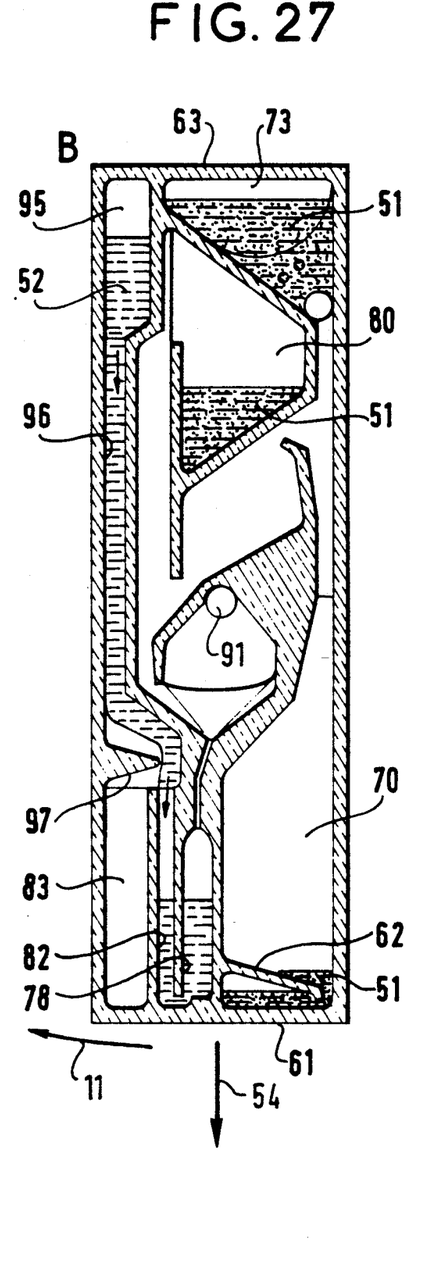
FIGS. 27 to 30 show the various implementation stages of a preparation cartridge for delivering a second dose of plasma.
Figure 28:
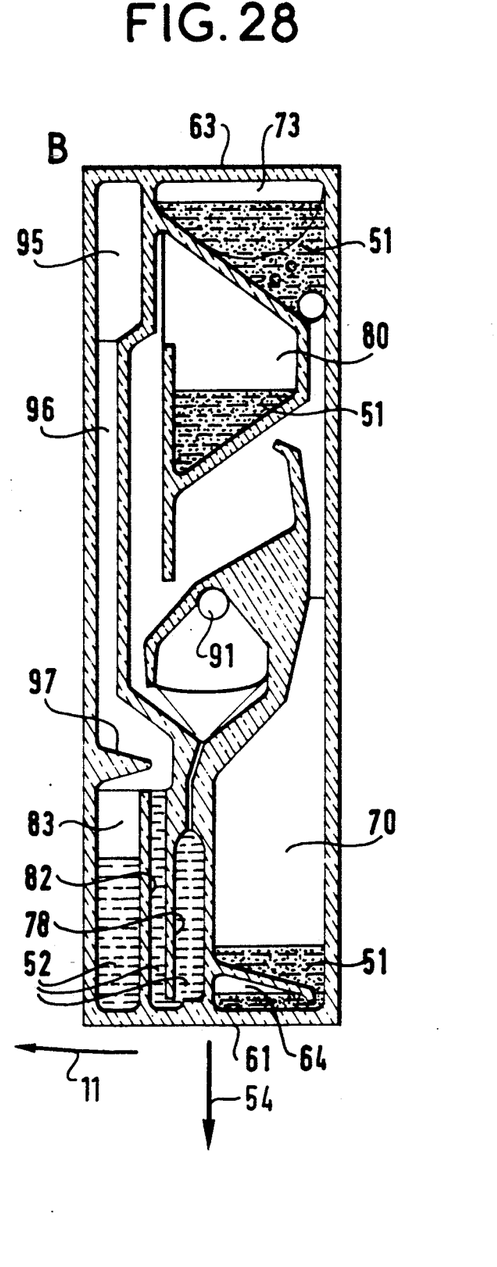

However, the cartridges 60 still contain a supply of plasma and are still capable of delivering a second calibrated dose for analysis by reaction cartridges 40'. In order to deliver this second dose, the cartridge 60 is returned to position B (FIG. 3B). The plasma 52 present in the receptacle 95 travels via the duct 96 and fills the cell 82 and the measurement cell 78. The chicane or baffle 97 prevents the plasma from penetrating into the cell 83 earlier on (FIG. 27). FIG. 8 illustrates the end of this stage.

Figure 29:
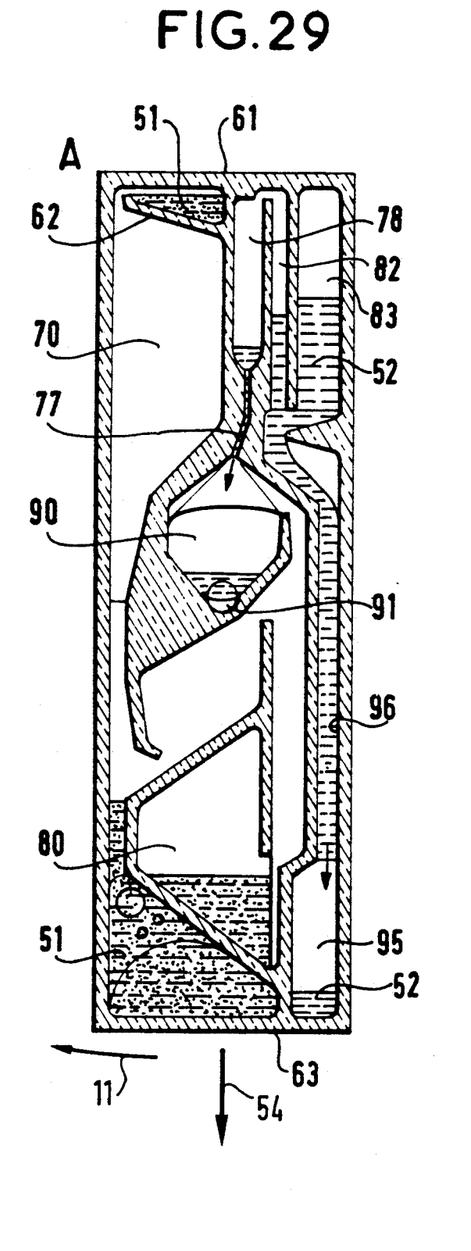
Figure 30:
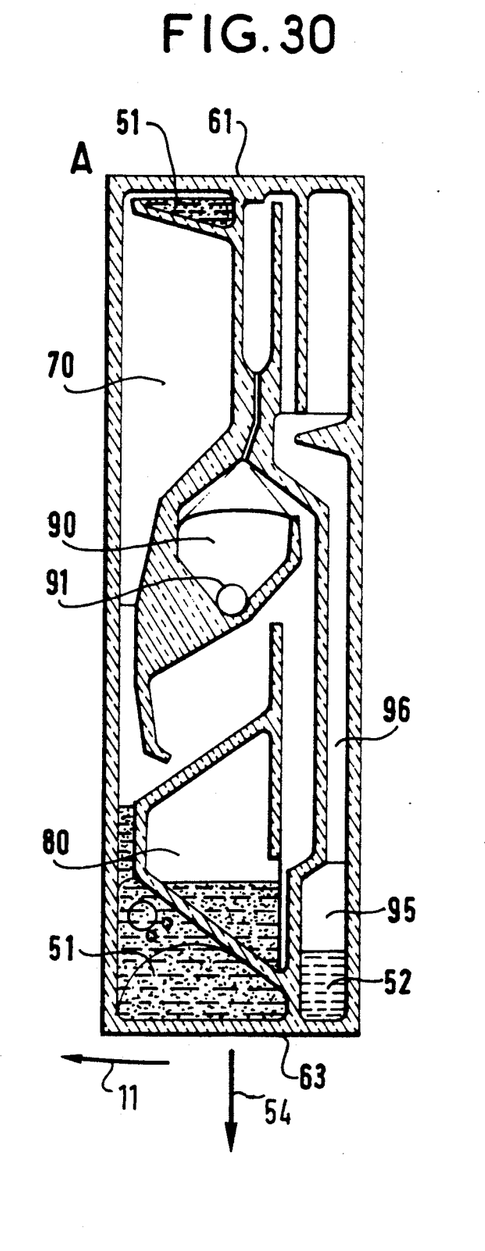

Finally, the cartridge is returned to position A. Turntable 4 is rotated so that the cartridges 40' come into alignment with the cartridges 60, and pressure is applied to the knob 32. This returns to the situation illustrated in FIGS. 20 and 21. There is an evacuation phase as illustrated in FIGS. 29 and 30. Thereafter the operations illustrated in FIGS. 22 to 26 are repeated, only this time using the cartridges 40'.

Apart from inserting the cartridges and lowering the top turntable, all other operations are under the control of a computer which may also be small in size. The results delivered by the reader module appear on a small printer.

By way of example, the two cartridge-carrying turntables may occupy a volume of 18 cm×18 cm×5 cm high. Each cartridge 40 may include ten reaction tubes.

This miniature laboratory can analyze three blood samples simultaneously, and for each of them it can perform two series of ten tests. It is also possible to perform forty tests on one sample and twenty on another, or indeed sixty tests on a single sample.

The above-described miniature laboratory has the following advantages in particular:
it is simple to manipulate;
it is flexible in operation;
results are obtained quickly;
it is compact; and
it is cheap.

With respect to simplicity of operation: the operator merely has to place cartridges corresponding to the tests required into the apparatus, then insert the liquid to be analyzed, then switch on the apparatus, and finally remove the sheet of paper on which the results are printed. Once analysis has been completed, the operator also has to remove the used cartridges.

With respect to flexibility in utilization, since each cartridge has ten tubes, the manufacturer has a wide range of options available for setting up desirable batteries of tests.

As for the speed with which results are obtained, the average waiting period before results are available for analyses performed simultaneously (on 3, 2, or 1 sample only) is less than ten minutes, with two of those minutes corresponding to performing the reactions.

As for compactness, a box containing the apparatus and a stock of cartridges does not weigh more than a few kilograms.

Naturally, the invention is not limited to the embodiment described and illustrated. The description relates to a sample of blood, however the miniature laboratory could also receive a sample of milk or any other emulsion or suspension.

The preparation cartridge may be arranged in such a manner as to deliver only one dose of plasma.

I claim:

1. A miniature laboratory for performing biological analyses by chemical reaction on a blood sample, wherein the laboratory comprises a block containing electronic and mechanical components, and supporting coaxially a top preparation turntable and a bottom analysis turntable;

said top preparation turntable being provided with radial housings for supporting preparation cartridges, each preparation cartridge acting to deliver at least one calibrated dose of plasma from a blood sample, said housings being capable of being rotated about their own centers;

said bottom analysis turntable being provided with a ring of recessed sectors suitable for supporting analysis cartridges, each analysis cartridge being closed by a lid having a breakable skin and each cartridge having an internal liquid-receiving compartment separated by a fragile wall from a peripheral distribution compartment adjacent to a plurality of vertical reaction tubes containing solid reagents;

said bottom turntable being slightly larger in diameter than the top turntable so as to leave said vertical reaction tubes visible;

and wherein the laboratory includes, in said block:

means for separately driving the two turntables, vertically spaced from each other, in rotation about their common axis, either slowly or for centrifuging;

said top turntable being provided with piercing members facing said breakable skins of said lids;

means for moving the top turntable into a position against the bottom turntable, with said piercing members piercing respective breakable skins to establish communication between the preparation cartridges and the liquid-receiving compartments of the analysis cartridges;

means for driving both turntables, constrained to rotate together, about their common axis;

means for breaking said fragile wall;

an optical analysis reader module situated level with the path of said reacting tubes; and a programmed microcomputer.

2. A miniature laboratory according to claim 1, wherein said top turntable is provided with three preparation cartridges each capable of delivering two calibrated doses of plasma, and wherein said bottom turntable is provided with six analysis cartridges, with the first three being intended for analyzing respective first doses and with the second three being intended for analyzing respective second doses.

3. A miniature laboratory according to claim 1, wherein each analysis cartridge includes about ten reaction tubes.

4. A miniature laboratory according to claim 1, wherein each analysis cartridge is stored in sealed manner with a diluant in its liquid-receiving compartment.

5. A miniature laboratory according to claim 1, wherein each preparation cartridge comprises a box closed by a lid, both said box and said lid being made of transparent plastic material, said box comprising first and second end faces and first and second longitudinally-extending side faces, and being compartmented in such a manner as to present:

a blood sample receiving receptacle running along said first longitudinally-extending side face from said first end face, followed by an outlet channel in which a plasma storage channel and a red corpuscle storage cell terminate; and a measurement cell running along said second longitudinally-extending side face going from said first end face, said measurement cell being connected by a capillary tube firstly to a central plasma evacuation cell having an outlet orifice in the bottom of said box, and secondly to an overflow channel opening out into said plasma storage cell and then into an overflow receptacle, the end of the measurement cell opposite to said capillary tube being connected by a capillary duct to overflow cells which also open out into said overflow channel.

6. A miniature laboratory according to claim 5, wherein said preparation cartridge also has a longitudinal channel against said second longitudinally-extending face and at the outlets from said overflow cells opposite from the outlet communicating with said measurement cell, said longitudinal channel opening out into a plasma storage receptacle situated close to said second end face.

* * * * *